US012773387B2

(12) United States Patent
Lee et al.

(10) Patent No.: US 12,773,387 B2
(45) Date of Patent: Oct. 27, 2026

(54) INJECTION FORMULATION COMPOSITION CONTAINING MESENCHYMAL STEM CELL-HYDROGEL AND METHOD FOR PREPARING, FREEZING AND DEFROSTING SAME

(71) Applicant: ANTEROGEN CO., LTD., Seoul (KR)

(72) Inventors: Sung-Koo Lee, Seoul (KR); Mi-Hyung Kim, Seoul (KR)

(73) Assignee: ANTEROGEN CO., LTD, Seoul (KR)

( * ) Notice: Subject to any disclaimer, the term of this patent is extended or adjusted under 35 U.S.C. 154(b) by 1131 days.

(21) Appl. No.: 17/437,306

(22) PCT Filed: Mar. 20, 2020

(86) PCT No.: PCT/KR2020/003878

§ 371 (c)(1),
(2) Date: Sep. 8, 2021

(87) PCT Pub. No.: WO2020/190094

PCT Pub. Date: Sep. 24, 2020

(65) Prior Publication Data

US 2022/0175666 A1 Jun. 9, 2022

(30) Foreign Application Priority Data

Mar. 21, 2019 (KR) ........................ 10-2019-0032490
Mar. 20, 2020 (KR) ........................ 10-2020-0034515

(51) Int. Cl.

| | |
|---|---|
| ***A61K 9/00*** | (2006.01) |
| ***A61K 9/16*** | (2006.01) |
| ***A61K 35/28*** | (2015.01) |
| ***A61P 19/02*** | (2006.01) |
| ***A61P 29/00*** | (2006.01) |
| ***C12N 11/04*** | (2006.01) |

(52) U.S. Cl.

CPC .......... *A61K 9/0024* (2013.01); *A61K 9/1658* (2013.01); *A61K 35/28* (2013.01); *A61P 19/02* (2018.01); *A61P 29/00* (2018.01); *C12N 11/04* (2013.01)

(58) Field of Classification Search

CPC combination set(s) only.
See application file for complete search history.

(56) References Cited

U.S. PATENT DOCUMENTS

| | | | | |
|---|---|---|---|---|
| 2008/0095749 A1* | 4/2008 | Aggarwal | ............... | A61P 17/06 424/93.7 |
| 2017/0304366 A1 | 10/2017 | Lee et al. | | |

FOREIGN PATENT DOCUMENTS

| | | |
|---|---|---|
| KR | 10684940 B1 | 2/2007 |
| KR | 1020090013425 B1 | 2/2009 |
| KR | 101289834 B1 | 7/2013 |
| KR | 101321144 B1 | 10/2013 |
| KR | 101407355 B1 | 6/2014 |
| KR | 101585032 B1 | 1/2016 |
| KR | 1020160034690 B1 | 3/2016 |
| KR | 101613478 B1 | 4/2016 |
| KR | 101687291 B1 | 12/2016 |
| KR | 101740298 B1 | 5/2017 |
| KR | 101814440 B1 | 1/2018 |
| KR | 1020180086378 B1 | 7/2018 |
| KR | 1020180123335 B1 | 11/2018 |
| WO | 2006/004951 A2 | 1/2006 |

OTHER PUBLICATIONS

Lima AC, Batista P, Valente TA, Silva AS, Correia IJ, Mano JF. Novel methodology based on biomimetic superhydrophobic substrates to immobilize cells and proteins in hydrogel spheres for applications in bone regeneration. Tissue Eng Part A. May 2013; 19(9-10):1175-87. (Year: 2013).*

"Injection." Merriam-Webster.com Dictionary, Merriam-Webster, https://www.merriam-webster.com/dictionary/injection. Accessed Nov. 18, 2024. (Year: 2024).*

Noori A, Ashrafi SJ, Vaez-Ghaemi R, Hatamian-Zaremi A, Webster TJ. A review of fibrin and fibrin composites for bone tissue engineering. Int J Nanomedicine. Jul. 12, 2017; 12:4937-4961. doi: 10.2147/IJN.S124671. PMID: 28761338; PMCID: PMC5516781. (Year: 2017).*

Lee et al., Biomaterials, 2010, vol. 31: 4926-4934. (Year: 2010).*

Lalegül-Ülker Ö, Şeker , Elçin AE, Elçin YM. Encapsulation of bone marrow-MSCs in PRP-derived fibrin microbeads and preliminary evaluation in a volumetric muscle loss injury rat model: modular muscle tissue engineering. Artif Cells Nanomed Biotechnol. Dec. 2019;47(1):10-21. (Year: 2019).*

International Search Report dated Jul. 29, 2020 for International Patent Application No. PCT/KR2020/003878 (Authorized officer, Unknown), 6 pages.

Catelas et al., "Human Mesenchymal Stem Cell Proliferation and Osteogenic Differentiation in Fibrin Gels in Vitro", Tissue Engineering, 2006, vol. 12, No. 8, pp. 2385-2396.

(Continued)

*Primary Examiner* — Fereydoun G Sajjadi
*Assistant Examiner* — Qinhua Gu
(74) *Attorney, Agent, or Firm* — MH2 Technology Law Group, LLP

(57) ABSTRACT

The present invention relates to a composition containing injectable mesenchymal stem cell-hydrogel and a method of preparing the same. Specifically, in a mesenchymal stem cell-hydrogel composition for injection prepared by a method of the present invention, since stem cells are attached to scaffolds in hydrogel beads, the stem cells are not easily lost or killed after the injection, and thus there is an advantage that an engraftment rate increases since the paracrine effect of the stem cells is continuously exhibited, and the stem cells are gradually released as hydrogel is degraded. In addition, the present invention has an advantage that healthy cells can be used without damages in cell membranes since injection formulation can be prepared without a treatment with proteolytic enzymes, and also a cryopreservation solution is easily removed from the mesenchymal stem cell-hydrogel beads even after freezing and thawing.

6 Claims, 6 Drawing Sheets

(56) References Cited

OTHER PUBLICATIONS

Eslani et al., "Corneal Mesenchymal Stromal Cells are Directly Antiangiogenic via PEDF and sFLT-1", IOVS, 2017, vol. 58, No. 12, pp. 5507-5517.

Wright et al., "Encapsulated Glucagon-Like Peptide-1-Producing Mesenchymal Stem Cells Have a Beneficial Effect on Failing Pig Hearts", Stem Cells Translational Medicine, 2012, vol. 1, pp. 759-769.

Bucher et al., "Nonviral Gene Delivery of Growth and Differentiation Factor 5 to Human Mesenchymal Stem Cells Injected into a 3D Bovine Intervertebral Disc Organ Culture System", Stem Cells International, 2013, vol. 2013, Article ID 326828, 9 pages.

Chabot et al., "Transient warming events occurring after freezing impairs umbilical cord-derived mesenchymal stromal cells functionality", Cytotherapy, 2017, vol. 19, No. 8, pp. 978-989.

Dashtdar et al., "Ultra-structural changes and expression of chondrogenic and hypertrophic genes during chondrogenic differentiation of mesenchymal stromal cells in alginate beads", PeerJ, 2016, 4:e1650 https://doi.org/10.7717/peerj.1650, 23 pages.

Fang et al., "Biocompatibility Studies on Fibrin Glue Cultured with Bone Marrow Mesenchymal Stem Cells in Vitro", Journal of Huazhong University of Science and Technology, 2004, vol. 24, No. 3, pp. 272-274.

Kim et al., "Fibrin Glue Improves the Therapeutic Effect of MSCs by Sustaining Survival and Paracrine Function", Tissue Engineering: Part A, 2013, vol. 19, No. 21 and 22, pp. 2373-2381.

Liao et al., "Combination of Guided Osteogenesis With Autologous Platelet-Rich Fibrin Glue and Mesenchymal Stem Cell for Mandibular Reconstruction", The Journal of Trauma® Injury, Infection, and Critical Care, 2011, vol. 70, No. 1, pp. 228-237.

Wang et al., "Fibrin Glue with Autogenic Bone Marrow Mesenchymal Stem Cells for Urethral Injury Repair in Rabbit Model", Tissue Engineering: Part A, 2012, vol. 18, No. 23 and 24, 11 pages.

Wu et al., "Fibrin glue as the cell-delivery vehicle for mesenchymal stromal cells in regenerative medicine", Cytotherapy, 2012, vol. 14, pp. 555-562.

* cited by examiner

INJECTION FORMULATION COMPOSITION CONTAINING MESENCHYMAL STEM CELL-HYDROGEL AND METHOD FOR PREPARING, FREEZING AND DEFROSTING SAME

CROSS-REFERENCE TO RELATED APPLICATIONS

This application is a U.S. National Stage application of PCT/KR2020/003878 filed 20 Mar. 2020, which claims priority to Korean Application No. 10-2019-0032490 filed 21 Mar. 2019 and Korean Application No. 10-2020-0034515 filed 20 Mar. 2020, the entire disclosures of which are hereby incorporated by reference in their entireties.

TECHNICAL FIELD

The present invention relates to an injectable mesenchymal stem cell-hydrogel composition, and a method of preparing, freezing and thawing the same, and specifically to a method of preparing stem cell-hydrogel in a constant form with a diameter of 5 mm or less to be developed into a formulation that can be easily filled into a syringe, cryopreserved, and immediately thawed to be used, if necessary.

Specifically, there has been a problem in that, when stem cells are injected into the body alone, the stem cells are easily lost at the injection site, and an engraftment rate is low. In the mesenchymal stem cell-hydrogel composition prepared by the method according to the present invention, since stem cells are attached to scaffolds in hydrogel beads, the stem cells are not easily lost or killed after the injection. Therefore, there is an advantage that an engraftment rate increases since the paracrine effect of the stem cells is continuously exhibited, and the stem cells are gradually released as hydrogel is degraded.

Another advantage of the preparation method of the present invention is that healthy cells can be used without damages in cell membranes since adhesive mesenchymal stem cells can be prepared into injection formulation without being treated with proteolytic enzymes. Another advantage is that a cryopreservation solution is easily removed from the mesenchymal stem cell-hydrogel beads after thawing.

BACKGROUND ART

A first-generation stem cell therapeutic agent in the related art non-selectively degrades all proteins exposed to cell membranes while the proteolytic enzymes are treated with isolated cells obtained by treating proteolytic enzymes such as trypsin or dispase. Therefore, intercellular bonding, basement membrane proteins, and the like are hardly maintained. An animal-derived material such as FBS is added to inactivate the proteolytic enzyme, and a washing-centrifugation process is performed several times to remove the animal-derived material. During one time of the washing-centrifugation process, 5% to 10% of cells are generally lost. Therefore, the cell collection process using proteolytic enzymes is a very inefficient method.

When isolated single cells are transplanted to a diseased site, the cells are released from a target site through diffusion, absorption and the like, and thus a proportion of settled cells is low. Since the mesenchymal stem cells are very adhesive cells, the mesenchymal stem cells are killed within 6 to 24 hours when being separated into single cells and have a very low engraftment rate.

WO2006/004951 discloses a method for creating soft tissues in predetermined shapes and sizes in de novo synthesis in vivo from adult mesenchymal stem cells (MSC) in a biocompatible scaffold, and a composition prepared by this method. The document presents a method of using a hydrogel polymer, more specifically polyethylene glycol diacrylate, as a biocompatible scaffold. However, the composition is intended for the restoration of soft tissue connections, the document merely presupposes that there should be little change in diameter when polyethylene glycol diacrylate is used as a scaffold, but does not disclose or imply a preparation process that enables immediate administration after the composition is cultured and filled into a syringe.

Korea Patent No. 1,289,834 discloses a cell therapeutic agent of regenerating a sphincter containing amniotic fluid-derived stem cells and presents that the cell therapeutic agent is injected into a hydrogel complex, specifically, alginate/PF-127/hyaluronic acid so that the effect is increased. However, the above document merely discloses a form prepared by injecting cell therapeutic agent into the hydrogel complex by mixing and injecting stem cells and hydrogel when using the same, but does not disclose a point of culturing stem cells in hydrogel beads.

Korean Patent No. 684,940 discloses a method for differentiating mesenchymal stem cells into chondrocytes, and more specifically discloses a method of culturing mesenchymal stem cells by fixing the mesenchymal stem cells to a mixed support containing fibrin/HA, which is a biodegradable polymer. However, the above document merely discloses that, when fibrin/HA is used as a support, even if TGF-beta, which is added for cell differentiation in the related art, is not added, the differentiation of mesenchymal stem cells into chondrocytes can be promoted.

Korean Patent No. 10-1814440 discloses a method of for stably mass-producing chondrocytes and cells having chondrogenic differentiation ability. More specifically, a method of uniformly mass-producing chondrocyte therapeutic agents without supports by processes of dispensing cells into a 96-well plate having a V-shaped bottom, culturing the cells in ultra-high density, and collecting pellets and transplanting the chondrocyte therapeutic agents into cartilage damaged sites is disclosed. However, the therapeutic agents are prepared into form of beads using only chondrocytes without supports, and thus there is a difference in composition from the present invention in which stem cells are cultured on a hydrogel bead support.

In the case of a method in the related art, a proteolytic enzyme treatment is performed in the process of preparing stem cell therapeutic agents. Therefore, there have been problems in that intercellular bonding and basement membrane protein may be damaged, cells may be lost in each step of a cell collection step, a washing step, a vial filling step, and a step of filling the syringe from the vial again, and most of active substances such as collagen synthesized during the cell culturing are removed because only single cells are collected and injected after enzyme treatment.

Meanwhile, in order to solve this problem, Korean Patent No. 10-1613478 discloses a method of making a hydrogel mass containing stem cells and filling a syringe with the hydrogel mass. However, there is a disadvantage in the course of filling the hydrogel mass into a syringe and injecting the hydrogel mass in that the shape of the hydrogel becomes irregular and the hydrogel mass does not have a consistent formulation. Also, the concentration of the hydrogel is limited in order to cause the hydrogel to have stiffness to a degree in which cells can be grown in a hydrogel scaffold and the hydrogel can be filled into a syringe.

Korean Patent No. 10-1687291 discloses a method of culturing stem cells or primary cultured cells by using a porous membrane and a hydrogel. More specifically, disclosed is a method of culturing cells in three dimensions by placing a porous membrane in a non-contact manner inside a cell culture vessel and coating a hydrogel thereon. However, the document merely discloses that the proliferation and growth of cells are increased in this system, but does not disclose that hydrogel containing cells is made and cultured in a bead form and the resultant can be administered after being filled into a syringe.

In order to solve this problem, recently, research on a method of putting cells or stem cells in a support to make the cells in a bead form has been conducted (Elizabeth et al., 2012; Christian et al., 2013; Havva et al., 2016; and Medi et al., 2017). As the type of the beads, alginate beads are most commonly used.

Korean Patent No. 10-1740298 discloses a method of preparing a hydrogel matrix containing cartilage-forming cells and a method for making the cells into beads. The above document presents a method of making an alginate solution and a chitosan solution and mixing the resultant with cartilage-forming cells to prepare a hydrogel matrix so that the cells are made into beads and cultured. However, disclosed is a study using general chondrocytes, not stem cells. Since the average size of the beads is adjusted by adjusting the diameter of a needle, the size of the beads cannot be made constant. Therefore, there is a limitation that the number of cells in the chondrocyte-hydrogel complex cannot be kept constant.

Korean Patent No. 10-1585032 discloses a method of mixing and culturing mesenchymal stem cells and a hydrogel solution and a method of filling a syringe with the same. However, there is a limitation that it is difficult to fill a desired number of cells into a syringe. On the other hand, the present invention has the advantage of being able to administer a desired number of cells to a cartilage damaged site by using a method of putting and culturing a certain number of cells in one bead.

It is important to make stem cells or cells in a form of beads and inject the stem cells or cells into the body, but freezing the stem cells or cells for storage for a long period of time and thawing the stem cells or cells anytime and anywhere as required to be easily used may also be an important factor in therapeutic agent development. Therefore, research on freezing and thawing methods to reduce cell damage and increase cell viability is in progress (Dominique et al. 2017).

Korean Patent Nos. 10-1321144 and 10-1407355 disclose a composition for cryopreserving stem cells. However, the document presents a method for increasing the cell viability when 2D cultured stem cells are frozen and thawed, and thus there is a difference from the present invention that presents a method for freezing and thawing a hydrogel-bead cell mixture.

For a stem cell therapeutic agent that is cryopreserved to be used in the related art, there is no specific method for removing a cryopreservation solution after thawing, and thus a method of injecting the stem cell therapeutic agent together with the cryopreservation solution is used. In this case, there has been a problem in that DMSO, that is a cryopreservation solution component, may cause various side effects in the body. The hydrogel-bead cell mixture according to the present invention has a size of about 0.1 to 5 mm, and thus has an advantage that the cryopreservation solution can be removed by a physically simple method.

Therefore, the present invention develops a formulation that is easy to be filled into a syringe by preparing a stem cell-hydrogel in a constant shape with a diameter of 5 mm or less, and the fact that the physical properties or physical strength of the injectable formulation used as a therapeutic agent by being frozen and thawed can be variously adjusted according to purposes and thus the injectable formulation can be used according to various therapeutic purposes is newly clarified so that the present invention is completed.

SUMMARY OF INVENTION

Technical Problem

The present invention provides a composition containing an injectable stem cell-hydrogel which is easily filled into a syringe by preparing a stem cell-hydrogel in a constant form to have a diameter of 5 mm or less, from which a cryopreservation solution can be removed by a physically simple method, and which is a ready-made preparation capable of being cryopreserved for a long period of time, and a preparation method thereof.

The present invention is to provide a method of preventing, treating, or improving musculoskeletal diseases, fistula diseases, or inflammatory diseases that includes a step of administering a composition containing a pharmaceutically effective amount of a stem cell-hydrogel to an individual.

Also, the present invention is to provide a use of a composition containing a stem cell-hydrogel for using a pharmaceutical composition for preventing or treating musculoskeletal diseases, fistula diseases, or inflammatory diseases.

Solution to Problem

The present invention provides a cell-hydrogel composition including cells; and hydrogel, in which the cell-hydrogel composition has a bead form.

The present invention provides a method of preparing a cell-hydrogel composition, including:

(a) a step of culturing cells;

(b) a step of mixing the cultured cells and a hydrogel solution to form a cell hydrogel bead; and (c) a step of culturing the cell hydrogel bead.

In addition, the present invention provides a method of preparing the cell-hydrogel composition according to the present invention further including a step of freezing and thawing the cell hydrogel bead.

In addition, the present invention provides a method of preventing or improving a musculoskeletal disease, a fistula disease, or an inflammatory disease, including a step of administering a pharmaceutically effective amount of the cell-hydrogel bead to an individual.

In addition, the present invention provides a method of treating a musculoskeletal disease, a fistula disease, or an inflammatory disease, including a step of administering a pharmaceutically effective amount of the cell-hydrogel bead to an individual.

In addition, the present invention provides a use of a cell-hydrogel composition as a pharmaceutical composition for preventing and treating a musculoskeletal disease, a fistula disease, or an inflammatory disease.

Advantageous Effects of Invention

In a mesenchymal stem cell-hydrogel composition for injection prepared by a method of the present invention, since stem cells are attached to scaffolds in hydrogel beads, the stem cells are not easily lost or killed after the injection, and thus there is an advantage that an engraftment rate increases since the paracrine effect of the stem cells is continuously exhibited, and the stem cells are gradually released as hydrogel is degraded. In addition, the present invention has an advantage that healthy cells can be used without damages in cell membranes since injection formulation can be prepared without a treatment with proteolytic enzymes, and also a cryopreservation solution is easily removed from the mesenchymal stem cell-hydrogel beads even after freezing and thawing.

y axis: relative value (fold increase).

Figure 5:
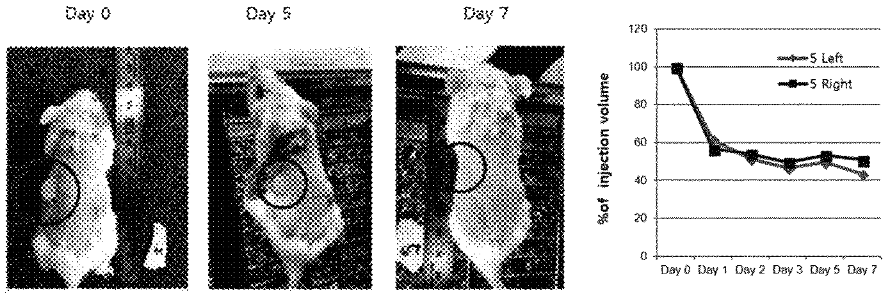

FIG. 5 is a view showing changes in volume for 7 days after subcutaneous injection of the cell-hydrogel bead of the present invention into a mouse.

Figure 6:
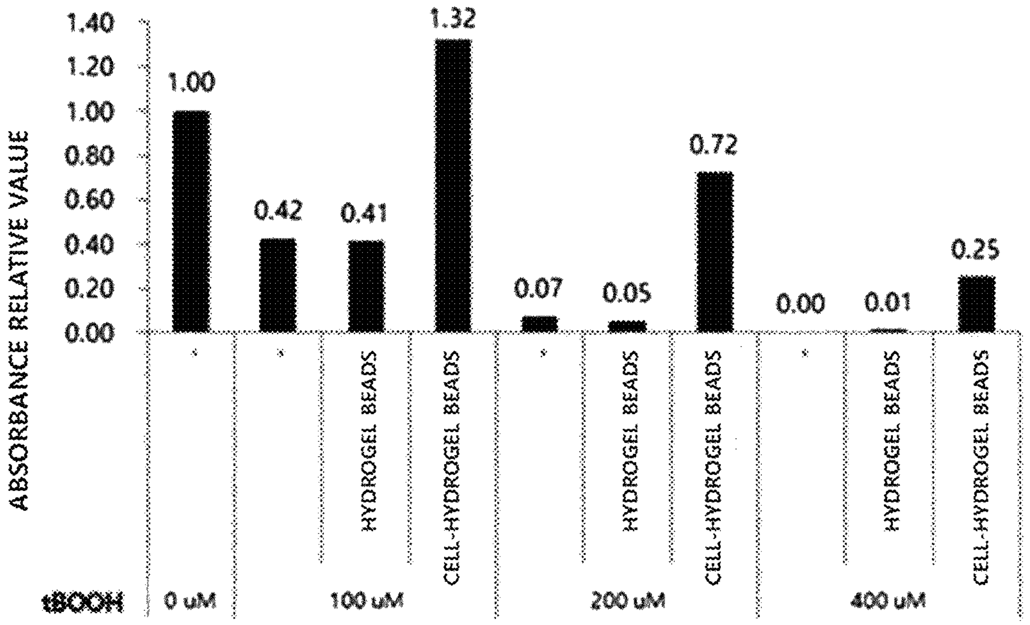

FIG. 6 is a view confirming a chondrocyte apoptosis inhibition effect due to oxidative stress of the cell-hydrogel bead of the present invention.

Figure 7:
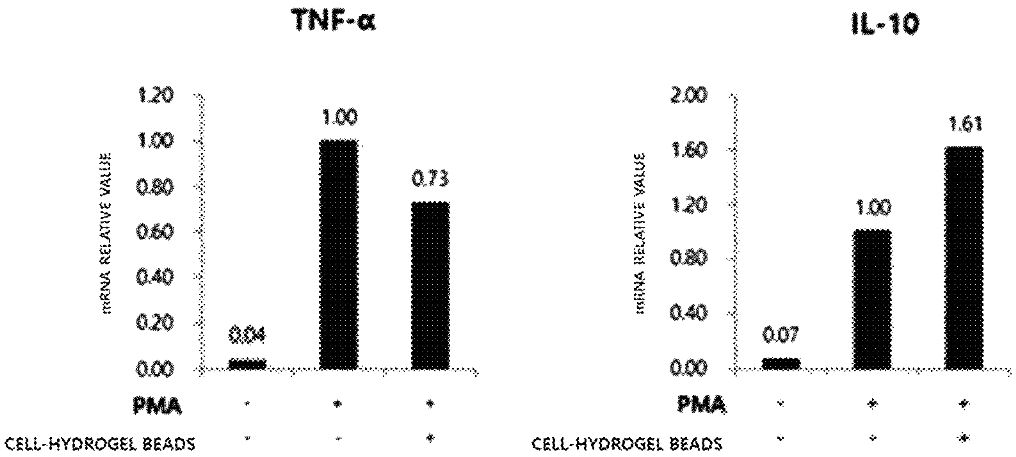

FIG. 7 is a view confirming an anti-inflammatory effect of the cell-hydrogel bead of the present invention.

DESCRIPTION OF EMBODIMENTS

Hereinafter, the present invention is specifically described.

The present invention provides a cell-hydrogel composition including cells; and hydrogel, in which the cell-hydrogel composition has a bead form.

The present invention provides a use of a cell-hydrogel composition including cells and hydrogel and having a bead form, as a pharmaceutical composition for preventing and treating a musculoskeletal disease, a fistula disease, or an inflammatory disease.

According to an aspect of the present invention, the diameter of the cell and the hydrogel is preferably 0.1 to 5 mm, more preferably 0.5 mm to 5 mm, and most preferably 1 mm to 4 mm.

According to an aspect of the present invention, the cell is preferably any one selected from the group consisting of a stem cell, a somatic cell, and a germ cell, but the present invention is not limited thereto.

According to an aspect of the present invention, the hydrogel is any one of two or more selected from the group consisting of fibrin glue, hyaluronic acid, gelatin, collagen, alginic acid, chitosan, cellulose, pectin, 2-hydroxyethyl methacrylate derivative or a copolymer thereof, polyethylene oxide, and polyvinyl alcohol, or two or more thereof.

According to an aspect of the present invention, the musculoskeletal disease is preferably any one selected from the group consisting of an injury of a joint, a bone disease, muscle weakness, myositis caused by a nerve damage of a joint, a myofascial pain syndrome, tendinitis, tenosynovitis, bursitis, ganglion tumor, carpal tunnel syndrome, Guyon's canal syndrome, wrist tendonitis, a hand-arm vibration syndrome, trigger finger, ganglion tumor, white finger, Raynaud's syndrome, lateral epicondylitis, medial epicondylitis, a radial tunnel syndrome, ulnar tunnel syndrome, olecranon bursitis, median nerve entrapment, a shoulder impingement syndrome, adhesive capsulitis, degenerative arthritis, turtle neck syndrome, cervical neuropathy, lumbar sprain, disc herniation, spondylolysis, spondylolisthesis, a degenerative lumbar disease, a degenerative disease, urinary incontinence, and a ligament and tendon damage, but the present invention is not limited thereto.

According to an aspect of the present invention, the fistula disease may be fistula Crohn's disease, but the present invention is not limited thereto.

According to an aspect of the present invention, the inflammatory disease is any one selected from the group consisting of atopic dermatitis, systemic lupus erythematosus, lupus, chilblain lupus, tuberculous lupus, lupus nephritis, dystrophic epidermolysis bullosa, psoriasis, rheumatoid fever, rheumatoid arthritis, back pain, fibromyalgia, myofascial disease, undifferentiated spondyloarthropathy, undifferentiated arthropathy, arthritis, inflammatory osteolysis, reactive arthritis, osteoarthritis, scleroderma, osteoporosis, chronic inflammatory disease caused by viral or bacterial infection, colitis, ulcerative colitis, inflammatory bowel disease, fungal infection, burns, a wound by a surgical or dental surgery, diabetic foot ulcer, type 1 diabetes, type 2 diabetes, ulcerative skin disease, sinusitis, rhinitis, conjunctivitis, asthma, dermatitis, inflammatory collagen vascular disease, glomerulonephritis, encephalitis, inflammatory enteritis, chronic obstructive pulmonary disease, sepsis, septic shock, pulmonary fibrosis, atherosclerosis, myocarditis, endocarditis, pericarditis, cystic fibrosis, Hashimoto's thyroiditis, Graves' disease, leprosy, syphilis, Lyme disease, borreliosis, neurogenic borreliosis, tuberculosis, sarcoidosis, macular degeneration, macular degeneration, uveitis, irritable bowel syndrome, Crohn's disease, Sjogren's syndrome, a chronic fatigue syndrome, chronic fatigue immunodeficiency syndrome, myalgic encephalomyelitis, amyotrophic lateral sclerosis, Parkinson's disease, and multiple sclerosis, but the present invention is not limited thereto.

The composition of the present invention exhibits a constant bead form having a diameter of 5 mm or less, and thus is easily filled into a syringe, and a cryopreservation solution can be removed by a physically simple method, so that DMSO that is the cryopreservation solution component that can cause various side effects in the body can be easily removed prior to administration. Specifically, in an example of a physically simple method, a cryopreservation solution and bead mixture are introduced into a syringe, a filter having a pore size of about 100 ul is mounted at the front end of the syringe, the solution is pushed, beads are caught in the filter, and only the cryopreservation solution can be removed.

In addition, after being filled into a syringe, the composition can be administered by transdermal injection, subcutaneous injection, intramuscular injection, submucosal injection, intraperitoneal injection, and the like.

In addition, in the present invention, the concentration of the hydrogel can be used without any particular limitation, can be adjusted according to various therapeutic purposes, and preferably contains fibrinogen at a concentration of 1.8 to 90 mg/mL.

The present invention provides a method of preparing a cell-hydrogel composition, including:

(a) a step of culturing cells;

(b) a step of mixing the cultured cells and a hydrogel solution to form a cell hydrogel bead; and (c) a step of culturing the cell hydrogel bead.

According to an aspect of the present invention, as the hydrogel, any one selected from the hydrogel group consisting of fibrin glue, hyaluronic acid, gelatin, collagen, alginic acid, chitosan, cellulose, pectin, 2-hydroxyethyl methacrylate derivative or a copolymer thereof, polyethylene oxide, and polyvinyl alcohol, or a complex of two or more thereof may be used, and more specifically, more specifically, fibrin glue may be used.

According to an aspect of the present invention, the fibrin glue may contain fibrinogen in a concentration of 1.8 to 90 mg/mL.

According to an aspect of the present invention, the cell hydrogel bead is preferably 0.1 to 5 mm, more preferably 0.5 mm to 5 mm, and most preferably 1 mm to 4 mm.

According to an aspect of the present invention, after the step (c), a step (d) of filling the cell-hydrogel composition into a syringe can be further included. The cell-hydrogel composition prepared by the preparation method according to the present invention can be directly administered locally using a needle of 10 to 25 gauges.

Meanwhile, in the method according to the present invention, after the cell hydrogel of the step (c) is cultured, a freezing and thawing step can be additionally added, and a cryopreservation solution can be removed by a physically simple method after the freezing and thawing.

When the cell-hydrogel composition of the present invention is used for injection, the physical properties or physical strength of the hydrogel can be variously adjusted and used according to purposes, and the hydrogel concentration is not specifically limited.

In a specific example of the present invention, the present inventors cultured human adipose-derived mesenchymal stem cells, added the mesenchymal stem cells into a thrombin solution, and dripped fibrinogen and the cell-thrombin solution each in an amount of 1 to 10 uL into a culture vessel by using a dispenser, respectively, to prepare fibrin glue hydrogel beads containing cells (hereinafter, referred to as cell-hydrogel beads) (see FIGS. 1A and 1B).

Figure 2:
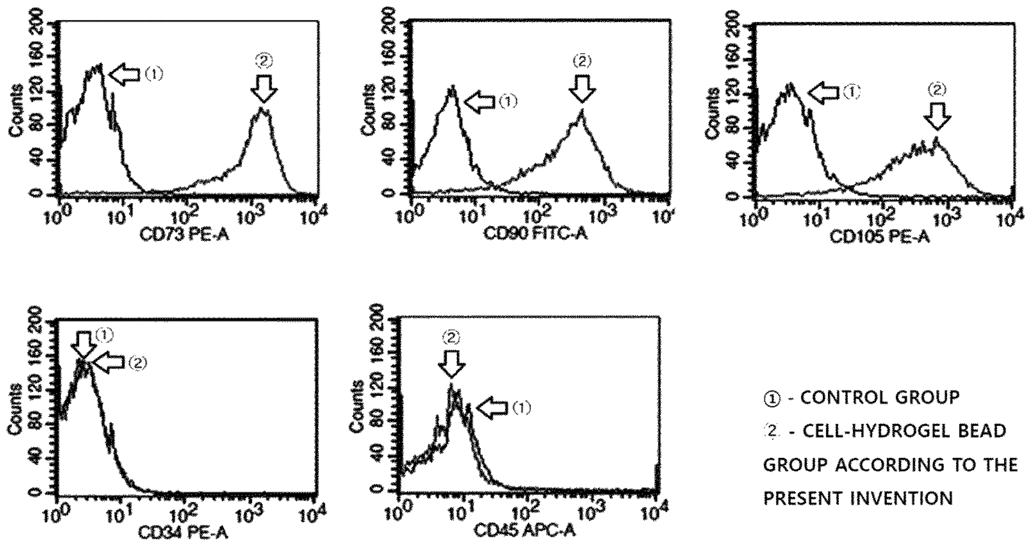
FIG. 2 is a view confirming cell characteristics in the cell-hydrogel bead.

As a result of checking the number of cells in a cell-hydrogel bead, viability, and characteristics of the cells, the present inventors confirmed that the cells cultured in a hydrogel bead according to the present invention confirmed immunological characteristics showing positive for CD73, CD90, and CD105 which were representative mesenchymal stem cell markers and showing negative for CD34 and CD45 which were hematopoietic cell markers were maintained (see Table 1, and FIG. 2).

Figure 3:
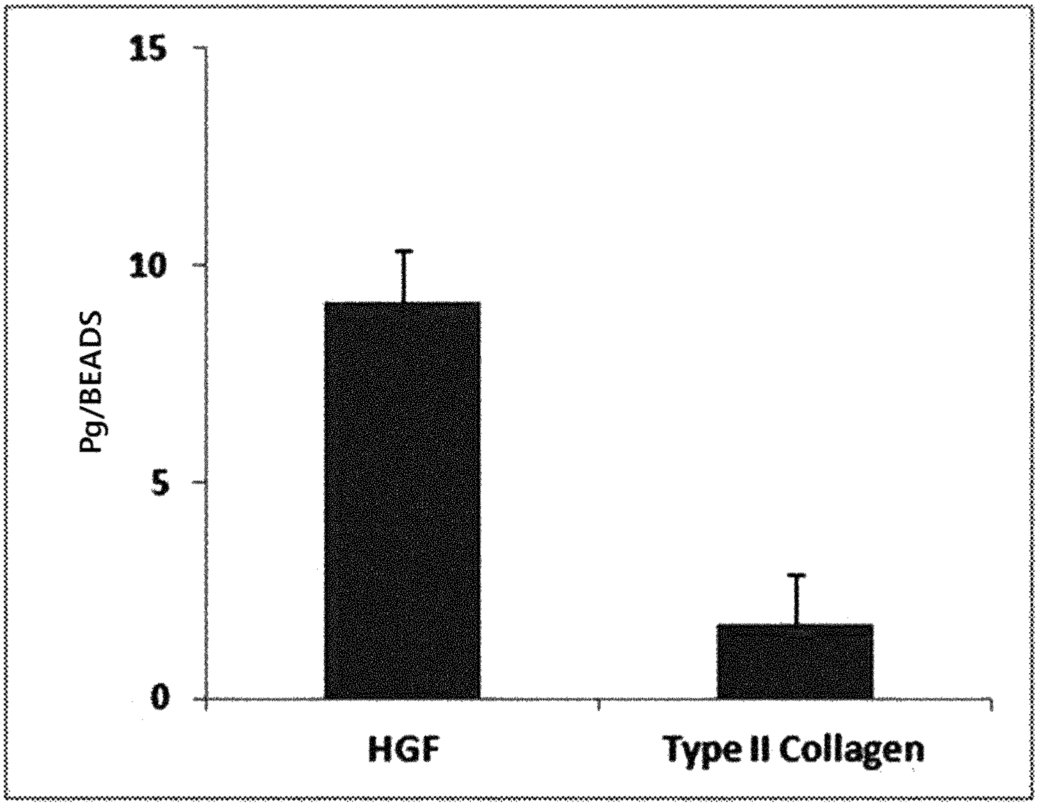
FIG. 3 is a view confirming an activating factor captured in the cell-hydrogel bead.

In addition, as a result of checking activating factors whether the activating factors secreted from the cell were captured in the bead in a cell-hydrogel bead preparation step, the present inventors confirmed that HGF and Type II Collagen secreted in the mesenchymal stem cells were significantly captured (see FIG. 3).

Figure 4:
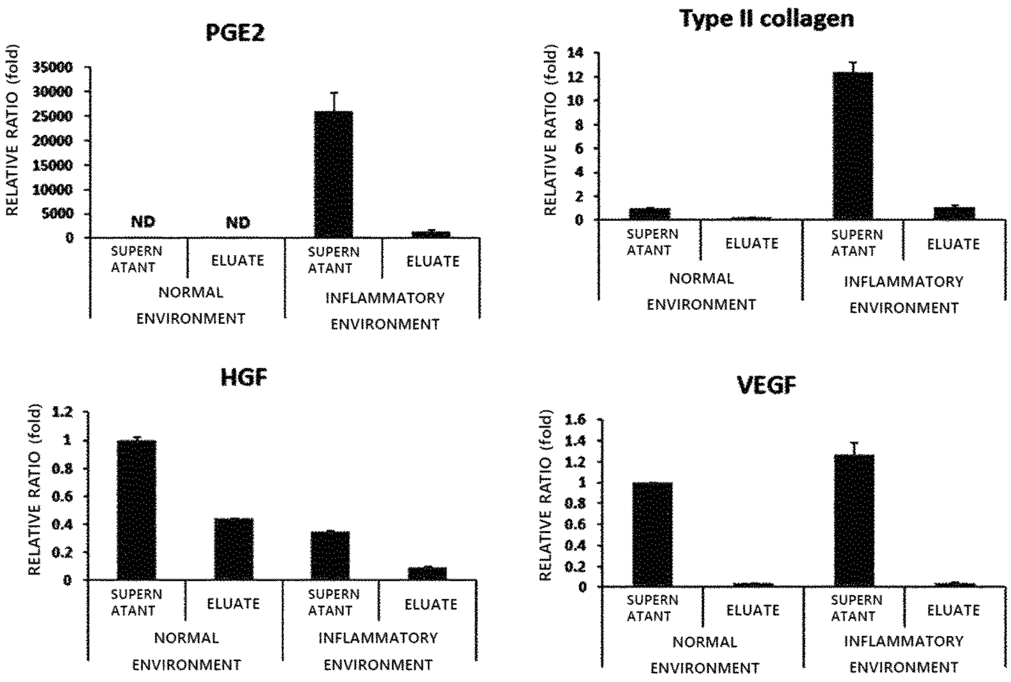
FIG. 4 is a diagram confirming the paracrine factor secretion effect of the cell-hydrogel bead.

As a result of checking a paracrine factor secretion effect of the cell-hydrogel beads, the present inventors confirmed that the cell-hydrogel bead of the present invention gradually secreted paracrine factors in an inflammatory environment induced with Interleukin 1β and exhibited significant therapeutic effects (see FIG. 4).

In the mesenchymal stem cell-hydrogel composition for injection prepared by the method of the present invention, the stem cells are attached to the scaffolds of the hydrogel beads, and thus the stem cells are not easily lost or killed after injection. Therefore, there is an advantage that an engraftment rate increases since the paracrine effect of the stem cells is continuously exhibited, and the stem cells are gradually released as hydrogel is degraded (see FIG. 5). In addition, there is an advantage that healthy cells can be used without damages in cell membranes since injection formulation can be prepared without a treatment with proteolytic enzymes, and also a cryopreservation solution is easily removed from the mesenchymal stem cell-hydrogel beads even after freezing and thawing.

In addition, the present invention provides a cell therapeutic agent for preventing and treating a musculoskeletal disease, a fistula disease, or an inflammatory disease which contains the composition according to the present invention as an active ingredient.

In the present invention, the term "cell therapeutic agent" refers to cells and tissues separated from humans and prepared by culture and special manipulation which are pharmaceuticals used for the purpose of treatment, diagnosis, and prevention. In particular, the term "cell therapeutic agent" refers to pharmaceuticals used for treatment, diagnosis and prevention by a series of actions such as proliferating and selecting live autologous, allogeneic, or xenogeneic cells in vitro in order to restore the function of cells or tissues or changing biological characteristics of cells by other methods. The cell therapeutic agent is largely classified into a somatic cell therapeutic agent and a stem cell therapeutic agent according to the degree of cell differentiation, and the present invention more specifically relates to an adipose-derived stem cell therapeutic agent.

In the present invention, the term "individual" refers to all animals including humans which have already developed or can develop a disease that can be prevented or treated by administration of the cell therapeutic agent according to the present invention.

The composition can be applied to various diseases such as an injury of a joint, a bone disease, muscle weakness, degenerative diseases caused by nerve damage in a joint, urinary incontinence, degenerative arthritis, ligament and tendon damage, diabetic foot ulcer, lower-extremity ischemic ulcers, and fistula disease.

In addition, the present invention provides a method of preventing or improving a musculoskeletal disease, a fistula disease, or an inflammatory disease, the method including a step of administering, to an individual, a cell-hydrogel composition containing cells and hydrogel in pharmaceutically effective amounts and having a bead form, and the cell and hydrogel have a diameter of 0.1 mm to 5 mm.

In addition, the present invention provides a method of treating a musculoskeletal disease, a fistula disease, or an inflammatory disease including a step of administering, to an individual, a cell-hydrogel composition containing cells and hydrogel, and having a bead form, and a diameter of the cell and the hydrogel is 0.1 mm to 5 mm, in pharmaceutically effective amounts.

The descriptions of the cell-hydrogel, the musculoskeletal disease, the fistula disease, and the inflammatory disease are the same as described for the cell-hydrogel composition, and thus specific descriptions thereof are incorporated herein by reference.

Meanwhile, in the mesenchymal stem cell-hydrogel composition for injection prepared by the method of the present invention, the stem cells are attached to the scaffolds of the hydrogel beads, and thus the stem cells are not easily lost or killed after injection. Therefore, there is an advantage that an engraftment rate increases since the paracrine effect of the stem cells is continuously exhibited, and the stem cells are gradually released as hydrogel is degraded. In addition, advantages that healthy cells can be used without damages in cell membranes since injection formulation can be prepared without a treatment with proteolytic enzymes, and also that a cryopreservation solution is easily removed from the mesenchymal stem cell-hydrogel beads even after freezing and thawing are confirmed. Therefore, the cell-hydrogel composition according to the present invention can be usefully used for preventing, treating, or improving a musculoskeletal disease, a fistula disease, or an inflammatory disease.

Hereinafter, the present invention is described in more detail through examples.

However, the following examples are provided for easier understanding of the present invention, and are not intended to limit the scope of the present invention thereto.

Example 1. Method of Culturing Human Adipose-Derived Mesenchymal Stem Cell

Adipose tissues can usually be obtained by liposuction, but the method is not limited thereto.

Adipose-derived mesenchymal stem cells were separated from adipose tissues obtained by liposuction as follows: adipose tissues were washed 3 to 4 times with an equal volume of PBS to remove the blood. A collagenase solution of the same volume as the adipose tissues was added and reacted in a water bath at 37° C. This was transferred to a centrifuge tube and centrifuged at 20° C. and 1,500 rpm for 10 minutes. The fat layer which was the supernatant was removed, and the collagenase solution which was the lower layer was carefully separated so as not to be shaken. The cell culture medium was added for suspension and then centrifuged at 20° C. and 1,200 rpm for 5 minutes. At this time, what was sunk to the bottom was a stroma-vascular fraction, and the supernatant was removed. The stroma-vascular fraction was suspended in a cell culture medium, inoculated into a culture vessel, and cultured at 37° C. in a 5%-$CO_2$ incubator for 24 hours. After removing the culture solution, the resultant was washed with a phosphate buffer solution, and was proliferated by using a cell culture medium or a culture medium containing cell growth factors such as a basic fibroblast growth factor (bFGF) or an epidermal growth factor (EGF) in a cell culture medium. When the adipose-derived mesenchymal stem cells grew to about 80% to 90% of the culture vessel, the mesenchymal stem cells were treated with trypsin to separate and obtain single cells.

Example 2. Preparing and Freezing Cell-Fibrin Glue Hydrogel Bead

1) Preparation of Cell-Fibrin Glue Hydrogel Bead 1 to $3\times10^5$ cells/mL of the adipose-derived mesenchymal stem cells obtained in Example 1 were added with a thrombin solution. 1.8 to 90 mg/mL of Fibrinogen was prepared. Fibrinogen and a cell-thrombin solution each in an amount of 1 to 10 uL were dripped into a culture vessel by using a dispenser to prepare fibrin glue hydrogel beads containing cells (hereinafter, referred to as cell-hydrogel beads).

2) Culture Vessel Attachment Culture Method

When the cell-hydrogel beads were completely hardened on the culture vessel, the cell culture medium was added without change, and then the resultant was cultured for 4 to 8 days in a 5%-$CO_2$ incubator at 37° C., and it was confirmed that a hemispherical shape is exhibited.

3) Suspension Culture Method

In addition, instead of the culture vessel attachment culture method of 2), a suspension culture method can be used. After the cell-hydrogel beads were completely hardened, the beads were removed from the bottom of the culture vessel and transferred to the culture vessel. The beads were suspended by adding a cell culture medium and cultured in a 5%-$CO_2$ incubator at 37° C. for 4 to 8 days. Meanwhile, in the case of the suspension culture, there is an advantage that culturing in a large volume is easy.

4) Washing and Freezing Cell-Hydrogel Beads

The culture medium was removed, and cell-hydrogel beads were collected from the culture vessel. The collected beads were mixed with human serum albumin containing 10% to 20% DMSO in a ratio of 1:1 and cryopreserved at −80° C.

Meanwhile, the cryopreservation solution and bead mixture were put into a syringe, a filter having a pore size of about 100 ul was mounted at the front end of the syringe, the solution was pushed, and then the beads were caught in the filter, so that only the cryopreservation solution was able to be removed in a physically simple method.

Figure 1A:
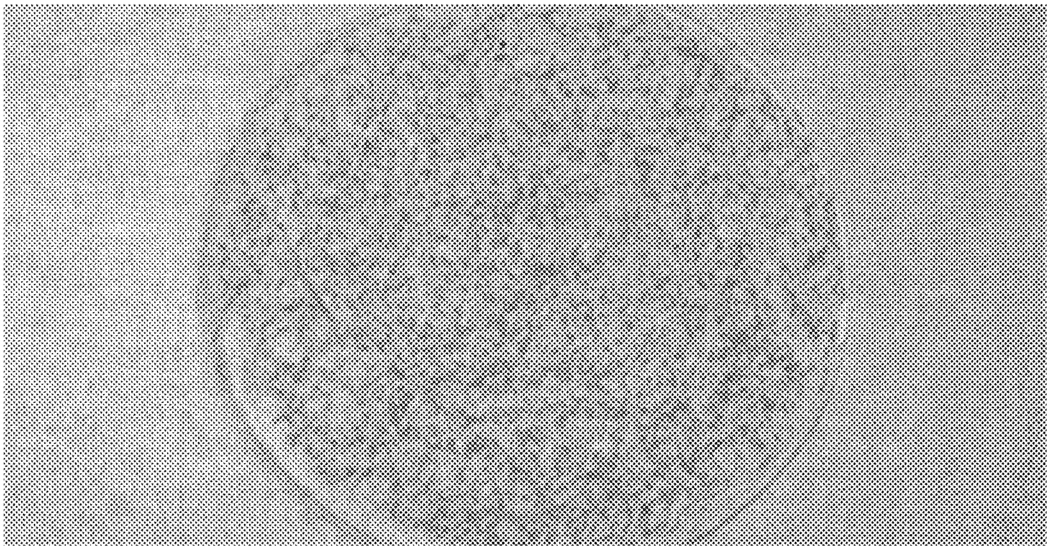
FIG. 1A is a view showing a photograph obtained by observing a cultured cells-hydrogel bead.

FIG. 1A is a photograph obtained by observing a cultured cells-hydrogel bead. It was confirmed that the diameter of the beads was 3 to 5 mm and that cells were proliferated well in the beads and were well compatible with the fibrin glue hydrogel.

Figure 1B:
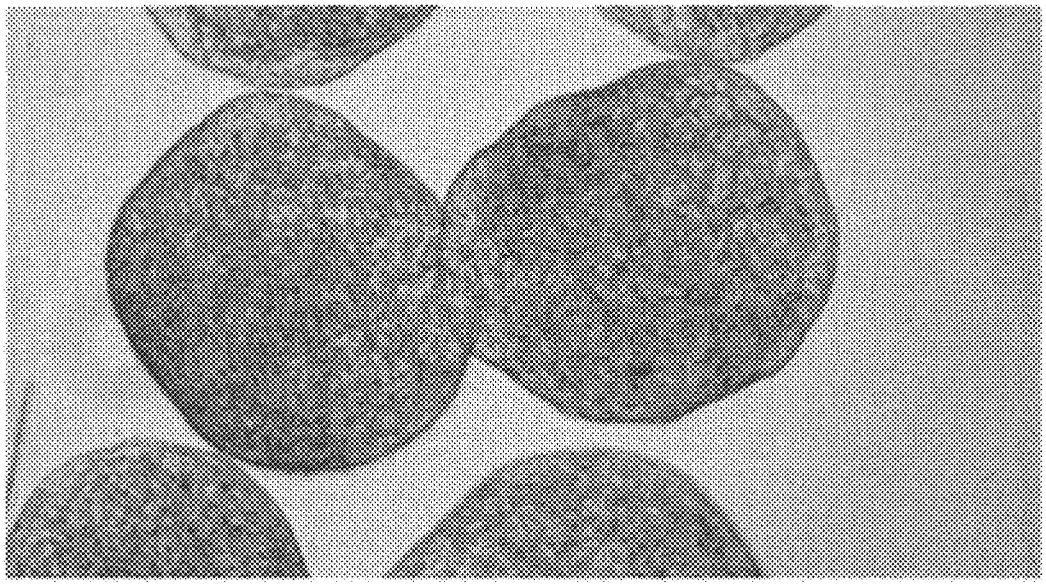
FIG. 1B is a view showing a micrograph of cell-hydrogel beads cryopreserved at −80° C., thawed, filled into a syringe, and sprayed by using a 17-gauge needle.

FIG. 1B is a view showing a micrograph of cell-hydrogel beads cryopreserved at −80° C., thawed, filled into a syringe, and sprayed by using a 17-gauge needle. It was confirmed that the shape and size of the beads were all kept constant even after freezing, thawing, and injecting using a needle.

Example 3. The Number of Cells in Cell-Hydrogel Bead, Viability, and Characteristics of Cells As a result of observing the cell-hydrogel bead cultured, washed, frozen, and thawed according to Example 2 under a microscope, it was confirmed that cells in the beads were homogeneously distributed (FIGS. 1A and 1B). Then, an enzyme was added to the cell-hydrogel bead cultured, washed, frozen, and thawed according to Example 2 to dissolve fibrin glue, and cells were obtained. As a result of analyzing the number of cells and the cell viability by staining the cells with trypan blue, about 15,000 cells were contained per bead, and the cell viability was 95% or more.

The obtained cells were stained with CD73, CD90, CD105, CD34, and CD45 and analyzed by flow cytometry. As a result, as shown in FIGS. 1A and 1B, it was confirmed that immunological characteristics in which the cells cultured in the hydrogel bead according to the present invention were positive for CD73, CD90, and CD105 that were representative mesenchymal stem cell markers and were negative for CD34 and CD45 that were hematopoietic cell markers were maintained (Table 1 and FIG. 2).

TABLE 1

| | |
|---|---|
| CD90 | 97.4 |
| CD73 | 98.8 |
| CD105 | 95.4 |
| CD45 | 1.4 |
| CD34 | 0.2 |

Example 4. Containing Activating Factor in Cell-Hydrogel Bead

It is known that mesenchymal stem cells secrete various activating factors during culture. Therefore, in order to check activating factors whether activators secreted in the cells in the cell-hydrogel bead preparation step were captured in the beads, an enzyme was added to the cell-hydrogel bead cultured, washed, frozen, and thawed according to Example 2 to obtain an eluate in which fibrin glue was dissolved, and the activating factors in the cell-hydrogel bead were analyzed.

As a result, as shown in FIG. 3, it was confirmed that about 10 pg of hepatocyte growth factors (HGF) that were representative activating factors secreted in the mesenchymal stem cell were captured per bead, and about 2 pg of Type II Collagen that was a major cartilage component was captured per bead (FIG. 3).

Example 5. Secretion of Paracrine Factor of Cell-Hydrogel Bead

It is known that mesenchymal stem cells have anti-inflammatory, anti-apoptotic, and cell proliferation promoting effects by a secretion action (paracrine action).

Accordingly, DMEM was added to the cell-hydrogel bead cultured, washed, frozen, and thawed according to Example 2, the resultant was cultured for 72 hours, an enzyme was added to the cell-hydrogel beads remaining after obtaining the culture supernatant, an eluate in which fibrin glue was dissolved was obtained, and the factors secreted from the cell-hydrogel beads were analyzed.

In addition, in order to create a microenvironment at a lesion site (inflammatory environment), a treatment with Interleukin 1β (Interleukin 1 beta; IL-1β) was performed, and the culture supernatant and the eluate were obtained in the same manner and analyzed.

As a result, as shown in FIG. 4, it was confirmed that, prostaglandin E2 (PGE2), known as a representative inflammatory regulator secreted from mesenchymal stem cells, was not secreted in a normal environment, but secretion was promoted in an inflammatory environment (FIG. 4).

In addition, it was confirmed that hepatocyte growth factors (HGF) and vascular endothelial growth factors (VEGF) that exhibit anti-inflammatory, anti-apoptotic, cell proliferation promotion, and angiogenesis promotion effects among representative growth factors secreted from mesenchymal stem cells were similarly secreted in both the normal environment and the inflammatory environment, and Type II Collagen that was major structural protein of articular cartilage, which was insufficiently secreted in the normal environment, rapidly increased in the inflammatory environment (FIG. 4).

Therefore, it was confirmed that the cell-hydrogel beads of the present invention can exhibit a significant therapeutic effect by gradually secreting paracrine factors when being administered to a lesion environment.

Example 6. Animal Test 30 cell-hydrogel beads cultured, washed, frozen, and thawed according to Example 2 were subcutaneously injected in two sites of on the left and right sides of a mouse, and volume changes were measured for seven days.

As a result, as shown in FIG. 5, it was confirmed that stem cells were not easily lost or killed even after subcutaneous injection, thus the paracrine effect of the stem cells was continuously exhibited, and the stem cells were gradually released as the hydrogel was degraded.

Example 7. Chondrocyte Apoptosis Inhibition Ability of Cell-Hydrogel Bead

It is known that osteoarthritis that is a representative musculoskeletal disease becomes worse as chondrocytes are killed. Accordingly, the chondrocyte apoptosis inhibition ability of the cell-hydrogel beads prepared according to Example 2 was confirmed.

Specifically, human chondrocytes were inoculated and attached to a 48-well plate, the cell-hydrogel beads prepared according to Example 2 and hydrogel beads without cells were added, and then the beads were co-cultured for 24 hours. Then, t-butyl hydroperoxide (tBOOH) was treated at concentrations of 100 μM, 200 μM, and 400 μM for 16 hours, respectively, to induce oxidative apoptosis of human chondrocytes. Thereafter, water soluble tetrazolium salt (WST-1) was added and cultured for about 3 hours, and then absorbance was measured to measure the number of living cells.

As a result, as shown in FIG. 6 and Table 2, it was confirmed that the cell-hydrogel beads inhibited apoptosis of chondrocytes due to oxidative stress (Table 2 and FIG. 6).

TABLE 2

| | tBOOH treatment | | | |
|---|---|---|---|---|
| | Concentration of 0 μM | Concentration of 100 μM | Concentration of 200 μM | Concentration of 400 μM |
| Untreated control group | 1.00 | 0.42 | 0.07 | 0.00 |
| Cell-hydrogel bead | 1.00 | 1.32 | 0.72 | 0.56 |
| Hydrogel bead | 1.00 | 0.41 | 0.05 | 0.01 |

Example 8. Anti-Inflammatory Macrophage Differentiation Promoting Ability of Cell-Hydrogel Beads Human monocytes were treated with phorbol 12-myristate 13-acetate (PMA) for 24 hours to induce differentiation into macrophages, then the cell-hydrogel beads prepared according to Example 2 were added, and the resultant was additionally cultured for 48 hours. Thereafter, the supernatant was collected, an amount of TNF-α secreted from activated M1 macrophages having pro-inflammatory characteristics and an amount of IL-10 secreted from activated M2 macrophages having anti-inflammatory characteristics were measured by enzyme-linked immunosorbent assay (ELISA).

As a result, as shown in FIG. 7, it was confirmed that when the amount of TNF-α secreted in case of adding PMA to human monocytes is 1.00, if the cell-hydrogel beads were further added thereto, the amount of TNF-α decreased to 0.73, while when the amount of IL-10 secreted in case of adding PMA is 1.00, if the cell-hydrogel beads were further added thereto, the amount of IL-10 increased to 1.61.

Therefore, it was confirmed that the cell-hydrogel beads have an effect of inhibiting the inflammatory reaction (FIG. 7).

INDUSTRIAL APPLICABILITY

The present invention relates to a composition containing injectable mesenchymal stem cell-hydrogel and a preparation method thereof. Specifically, in the mesenchymal stem cell-hydrogel composition for injection prepared by the method of the present invention, the stem cells are attached to the scaffolds of the hydrogel beads, and thus the stem cells are not easily lost or killed after injection. Therefore, there is an advantage that an engraftment rate increases since the paracrine effect of the stem cells is continuously exhibited, and the stem cells are gradually released as hydrogel is degraded. In addition, there is an advantage that healthy cells can be used without damages in cell membranes since injection formulation can be prepared without a treatment with proteolytic enzymes, and also, a cryopreservation solution is easily removed from the mesenchymal stem cell-hydrogel beads even after freezing and thawing, thus the mesenchymal stem cell-hydrogel composition can be usefully used.

The invention claimed is:

1. An injectable bead form cell-hydrogel composition comprising:

cells; and hydrogel, wherein the injectable bead form has a diameter of 0.1 mm to 5 mm, the cells are mesenchymal stem cells, and the cells are encapsulated inside the injectable bead form, the hydrogel is fibrin glue, and the fibrin glue contains fibrinogen at a concentration of 1.8 mg/mL to 90 mg/mL, and the injectable bead form cell-hydrogel composition keeps its bead form, cell morphology, and characteristics of the cells after freezing and thawing, compared to before freezing.

2. The composition according to claim 1, wherein the injectable bead form has a diameter of 1 mm to 4 mm.

3. A pharmaceutical composition for preventing or treating a musculoskeletal disease, a fistula disease, or an inflammatory disease comprising:

the composition according to claim 1 as an active ingredient.

4. The pharmaceutical composition for preventing or treating a musculoskeletal disease, a fistula disease, or an inflammatory disease according to claim 3, wherein the musculoskeletal disease is any one selected from the group consisting of an injury of a joint, an injury of a joint caused by a nerve damage of the joint, a bone disease, muscle weakness, myositis caused by a nerve damage of a joint, a myofascial pain syndrome, tendinitis, tenosynovitis, bursitis, ganglion tumor, a carpal tunnel syndrome, Guyon's canal syndrome, wrist tendonitis, a hand-arm vibration syndrome, trigger finger, white finger, Raynaud's syndrome, lateral epicondylitis, medial epicondylitis, ulnar tunnel syndrome, olecranon bursitis, median nerve entrapment, a shoulder impingement syndrome, adhesive capsulitis, degenerative arthritis, turtle neck syndrome, cervical neuropathy, lumbar sprain, disc herniation, spondylolysis, spondylolisthesis, a degenerative lumbar disease, a degenerative disease, urinary incontinence, and a ligament and tendon damage.

5. The pharmaceutical composition for preventing or treating a musculoskeletal disease, a fistula disease, or an inflammatory disease according to claim 3, wherein the inflammatory disease is any one selected from the group consisting of atopic dermatitis, systemic lupus erythematosus, lupus, chilblain lupus, tuberculous lupus, lupus nephritis, dystrophic epidermolysis bullosa, psoriasis, rheumatoid fever, rheumatoid arthritis, back pain, fibromyalgia, myofascial disease, undifferentiated spondyloarthropathy, undifferentiated arthropathy, arthritis, inflammatory osteolysis, reactive arthritis, osteoarthritis, scleroderma, osteoporosis, chronic inflammatory disease caused by viral or bacterial infection, colitis, ulcerative colitis, inflammatory bowel disease, fungal infection, burns, a wound by a surgical or dental surgery, diabetic foot ulcer, type 1 diabetes, type 2 diabetes, ulcerative skin disease, sinusitis, rhinitis, conjunctivitis, asthma, dermatitis, inflammatory collagen vascular disease, glomerulonephritis, encephalitis, inflammatory enteritis, chronic obstructive pulmonary disease, sepsis, septic shock, pericarditis, cystic fibrosis, Hashimoto's thyroiditis, Graves' disease, leprosy, syphilis, Lyme disease, borreliosis, neurogenic borreliosis, tuberculosis, sarcoidosis, macular degeneration, macular degeneration, uveitis, irritable bowel syndrome, Crohn's disease, Sjogren's syndrome, a chronic fatigue syndrome, chronic fatigue immunodeficiency syndrome, myalgic encephalomyelitis, amyotrophic lateral sclerosis, Parkinson's disease, and multiple sclerosis.

6. The composition according to claim 1, wherein the composition is formulated for administration by any one selected from the group consisting of transdermal injection, subcutaneous injection, intramuscular injection, submucosal injection, and intraperitoneal injection.

* * * * *